(12) United States Patent
Leonard et al.

(10) Patent No.: US 6,890,755 B1
(45) Date of Patent: May 10, 2005

(54) RECOVERY OF FETAL CELLS FROM MATERNAL BLOOD USING CHAOTIC ADVECTION

(75) Inventors: Edward F. Leonard, Bronxville, NY (US); Rene Chevray, Port Jefferson, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/986,552

(22) Filed: Dec. 8, 1997

(51) Int. Cl.[7] .................................................. C12N 5/08
(52) U.S. Cl. ...................... 435/372; 435/261; 435/394; 435/286.7; 210/787
(58) Field of Search ................................. 210/787, 645, 210/79.9; 435/394, 372, 261, 286.7

(56) References Cited

U.S. PATENT DOCUMENTS

| | | | | |
|---|---|---|---|---|
| 4,675,286 A | * | 6/1987 | Calenoff | 435/7.21 |
| 5,275,933 A | * | 1/1994 | Teng et al. | 435/2 |
| 5,447,842 A | * | 9/1995 | Simons | 435/6 |
| 5,639,669 A | * | 6/1997 | Ledley | 436/177 |
| 5,684,712 A | * | 11/1997 | Goffe et al. | 700/285 |

OTHER PUBLICATIONS

Chaiken et al., "Experimental Study of Lagrangian Turbulence in a Stokes Flow," Proc. R. Soc. Lond. A408:165–174 (1986).

Gomez, 1999 "Attachment of Cells to Surfaces under Controlled Fluid Flows," Graduate Thesis, Columbia University.

* cited by examiner

Primary Examiner—David A. Redding
(74) Attorney, Agent, or Firm—Baker Botts L.L.P.

(57) ABSTRACT

To extract fetal cells from a sample of maternal blood or a fluid derived from maternal blood, sample liquid is moved over a collector surface bearing a ligand for the fetal cells. Chaotic advection in the liquid enhances the efficiency of cell collection.

6 Claims, 1 Drawing Sheet

RECOVERY OF FETAL CELLS FROM MATERNAL BLOOD USING CHAOTIC ADVECTION

TECHNICAL FIELD

This invention relates to the recovery of fetal cells from the maternal circulation and, more particularly, to recovery using advection of cells on a collector surface.

BACKGROUND OF THE INVENTION

In pregnancy, for diagnostic purposes, fetal cells can be obtained by methods such as amniocentesis or chorionic villus sampling. With such methods, it is relatively easy to obtain a significant sample for diagnostic analysis, so that diagnosis is highly reliable. But, because they require invasion of the uterus, these methods pose a risk especially to the fetus.

Fetal cells are present also in the maternal circulation. Thus, in principle, a maternal blood sample may be used for fetal diagnosis, obtained by venipuncture. However, because of the low concentration of fetal cells, it is difficult to extract a significant sample of fetal cells from maternal blood.

SUMMARY OF THE INVENTION

To extract fetal cells from a sample of maternal blood or a fluid derived from maternal blood, sample liquid is moved over a collector surface bearing a ligand for the fetal cells. Chaotic advection in the liquid enhances the efficiency of cell collection.

DETAILED DESCRIPTION

Practical isolation of fetal cells from the maternal circulation is complicated by factors such as (1) the scarcity of the fetal cell population which is roughly 1:100,000, (2) ambiguities in the specific identification of fetal cells through an appropriate cell surface marker, and (3) uncertain specifications for yield, freedom from contamination by irrelevant cell types, and suitability of recovered cells for cytogenetic analysis. These practical considerations give rise to issues which may be termed as "macroscopic" or "microscopic", respectively, to be resolved for successful isolation. The macroscopic issue concerns adequacy of mixing for delivering cells from throughout a volume to a collecting surface. Also, the total collector area must be small enough to require only minimal dilution of captured cells during their subsequent elution from the collector. The microscopic issue is with establishing an optimum local environment for cell capture, and with the minimization of bond-disrupting forces.

In a technique based on collecting cells onto a surface, there is competition between macroscopic conditions that optimize transport between cell suspension and a collector, and microscopic conditions that optimize the actual fixation of cells onto the collector. An advantage of the chaotic advection technique of the invention lies in a significant reduction in the competition between macroscopic and microscopic requirements. As a result, capture of ligand-sensitive cells is maximized without requiring strong agitation of the liquid. Strong agitation, resulting in a turbulent flow, is precluded in view of the delicate nature of the fetal cells.

Chaotic advection may be defined in terms of fluid flow, with a fluid flow being termed "chaotic" if it is piece-wise steady over time, but includes transitions between different steady flows. Steady flows, with flow conditions such as pressure and velocity remaining constant at each point of a flow, are also known as laminar or streamline flows. In contrast to a strictly laminar flow, repeatedly switching from one laminar flow to another as in a chaotic flow results in enhanced mixing of the fluid. Accordingly, for present purposes, chaotic advection means transport in a chaotic flow. Chaotic advection can be effected in apparatus according to FIG. 1, for example.

Figure 1:
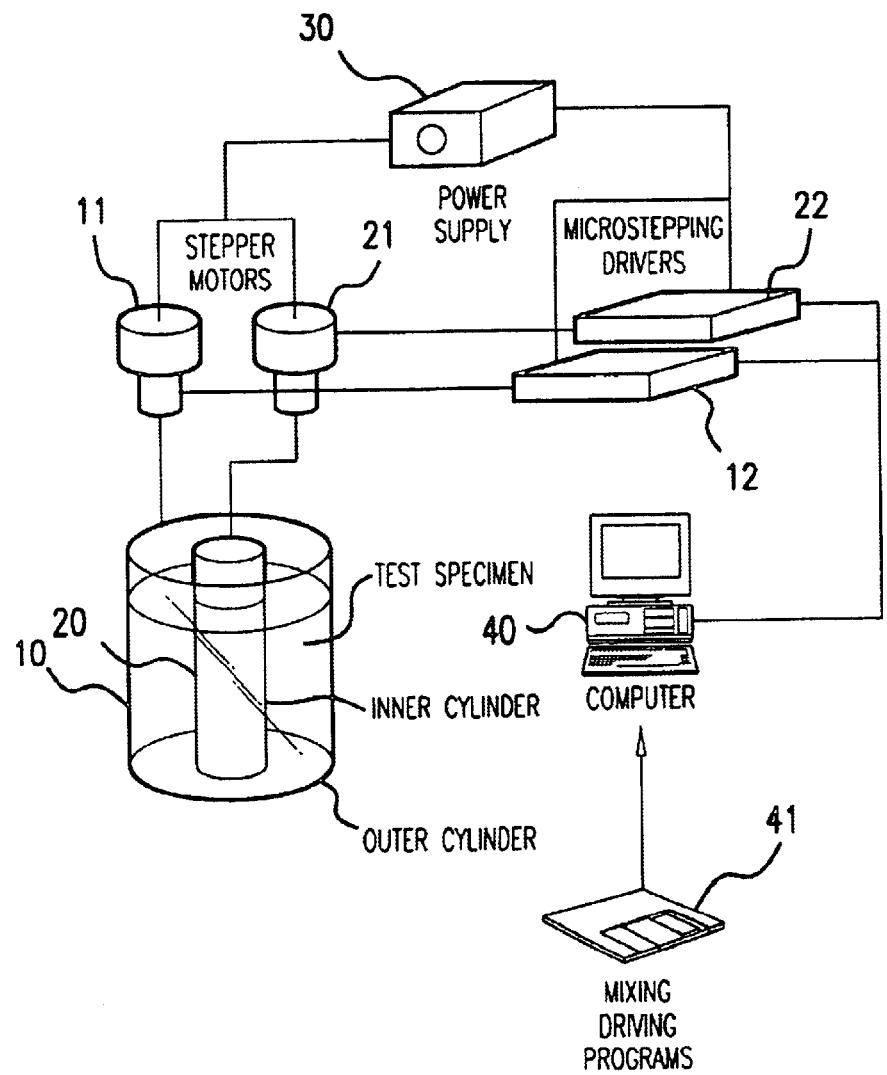
FIG. 1 is a schematic of apparatus as can be used in extracting fetal cells from maternal blood or a fluid derived from maternal blood, using chaotic advection.

FIG. 1 shows a cylindrical vessel 10 and a cylindrical rod 20 which is disposed eccentric with respect to the vessel 10. The space between the vessel 10 and the rod 20 can receive a liquid specimen from which fetal cells are to be collected. The vessel 10 and/or the rod 20 is coated at least in part with a ligand for the fetal cells. Alternatively, one or several separate collectors can be immersed in the specimen, coated at least in part with the ligand. Such collectors may take the form of fibers, for example. Specific to the transferrin receptor on human fetal nucleated erythrocytes, anti-CD71 can be used as ligand, for example.

The vessel 10 and the rod 20 have respective drive units 11 and 21, for rotating the vessel 10 and the rod 20 independently. FIG. 1 further shows a power supply 30 for the drive units 11 and 21, respective drivers 12 and 22, a computer 40, and a source 41 of software for the computer. With the software, the computer 40 is programmed to control the drivers 12 and 22 such that fluid flow is chaotic.

In an experimental arrangement, the vessel 10 has an inner diameter of 9.2 mm, and the rod 20 an outer diameter of 2.875 mm. The holding volume between the vessel 1 and the rod 20 is approximately 10 ml. The vessel 10 is made of transparent Lucite; the rod 20 is a solid steel rod. Each of the drive units 11 and 12 is a high-resolution stepper motor having a speed range from 0.6 to 6.0 rpm. The computer is an IBM 286-compatible PC, programmed for modulating rotation rates.

With the experimental arrangement, as the bottom of the vessel 10 is transparent, flow in the vessel can be visualized and recorded by a high-resolution video capture system. A Panasonic CCD camera model No. WV F2 and a portable recorder Panasonic AG 2400 were used.

Exemplary operating conditions are as follows: a rotation rate of 1 $min^{-1}$ for a duration of 5 seconds, of the vessel 10 and the cylinder 20 in an alternating fashion, for a total duration of 1 hour.

Figure 2:
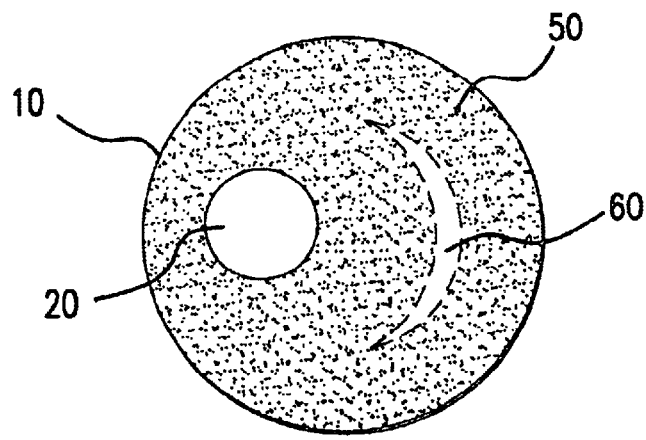
FIG. 2 is a cross section of an exemplary volume of liquid, with a stippled region in which flow is chaotic as determined by computer simulation.

FIG. 2 shows the vessel 10 and the cylinder 20 in cross section. As determined by computer simulation, in an exemplary chaotic flow generated by alternately rotating the vessel 10 and the cylinder 20, the stippled region 50 undergoes chaotic mixing while the complementary lenticular region 60 remains isolated from the chaotic flow. For optimized yield of fetal cells reaching the vessel 10 or the cylinder 20 out of the liquid disposed in the vessel, the area of region 60 is minimized.

In the configuration according to FIG. 1, with parallel axes of the cylindrical vessel 10 and the cylindrical rod 20 resulting in a two-dimensional flow, it is essential that the two axes be distinct rather than coincident. Otherwise, even when alternating between inner and outer rotation, the flow will remain strictly laminar rather than chaotic. As an alternative to the configuration according to FIG. 1, a cylindrical outer vessel in combination with a cylindrical inner rod can be disposed also with axes disposed other than vertical, e.g. horizontal. In still other configurations, a chaotic flow need not be spatially two-dimensional, but have fluid particles travel in three spatial dimensions.

Fetal cells that are candidates for capture and analysis include nucleated erythrocytes, trophoblasts and leucocytes in the maternal circulation. Nucleated erythrocyte is of particular interest, as it is predominant in early fetal blood, scarce in the adult circulation, and not traceable to a previous pregnancy.

In experiments, murine (mouse) lymphocytes were used, in the absence of irrelevant cells, and using as the collecting ligand a murine anti common leukocyte antigen, CD-45. The ability to capture cells relies on the ability to find a specific ligand with high affinity to a marker that is on the cell surface in sufficient numbers. The ligand-marker bond must be reversible without cell damage to permit recovery of cells for cytogenetic analysis.

The specific experimental system is based on murine TA3 hybridoma B lymphocytes originally from the laboratory of Dr. Roderick Nairn, University of Michigan, Department of Microbiology and Immunology. This system provides a relatively homogenous test cell population and allows for small turnover time between experiments. For rapid detection, cells are labeled with a fluorescent cytoplasmic dye, BCECF-AM, Molecular Probes, and counted under a fluorescent microscope while still attached to the collector surface.

In the experiments, the rod 20 was used as collector. This choice is convenient, and has been shown by computation to be suitable. For coating, the rod 20 was dipped in a solution of 2% polystyrene in toluene, and air dried. This coating was chosen because polystyrene is the most common surface on which to deposit antibodies preparatory to cell separation. The coating quality was checked by measurement of the electrical conductivity between the rod and a conducting solution in which it is immersed.

The coated rod 20 was then coated further with antibody or, in control experiments, with BSA as a control. The interior of the vessel 10 was routinely coated with BSA in order to prevent binding there. A suspension of dyed cells with total volume 10 ml was placed in the chamber, and the vessel 10 and rod 20 were rotated for a prescribed number of cycles under computer control. Rotational velocities were maintained such that the shear rate was less than 5 $sec^{-1}$. At the completion of the run, the rod 20 was removed, placed on a stand, and the surface was inspected for cells under a fluorescence microscope.

Regardless of whether the vessel 10 or the rod 20 is rotated, the flow streamlines in the vicinity of the rod 20 are nearly parallel to the cylinder surface of the rod 20. As a result, collection of cells at the surface of the rod 20 may be less efficient as compared with other locations in the flow.

We claim:

1. A method for collecting fetal cells from a maternal blood sample, comprising the steps of:
    disposing a liquid comprising the maternal blood sample in a vessel having (i) an interior comprising a movable outer portion and a movable inner portion and (ii) a collector surface bearing a ligand specific for the fetal cells; and
    effecting a chaotic flow in the liquid by alternately moving the outer portion and inner portion of the vessel relative to each other so as to repeatedly switch from one laminar flow to another for a duration of time effective for binding fetal cells to the ligand on the collector surface.

2. The method according to claim 1, wherein the vessel comprises a rotatable outer portion and a rotatable inner portion whose axes of rotation are distinct rather than coincident.

3. The method according to claim 2, wherein the step of effecting the chaotic flow comprises rotating each of the outer and inner portions of the vessel in an alternating fashion.

4. The method according to claim 1, wherein the collector surface is disposed at the outer portion of the vessel.

5. The method according to claim 1, wherein the collector surface is disposed at the inner portion of the vessel.

6. The method according to claim 1, wherein the collector surface is disposed on at least one surface immersed in the liquid.

* * * * *